United States Patent
Zimmerman et al.

(10) Patent No.: US 8,095,378 B2
(45) Date of Patent: Jan. 10, 2012

(54) AUTOMATED SYSTEM FOR MANAGING THE SELECTION OF CLINICAL ITEMS AND DOCUMENTATION FOR A CLINICAL EVENT

(75) Inventors: Michael A. Zimmerman, Kansas City, MO (US); Melissa A. Morawitz, Independence, MO (US); Lawrence J. Licata, Olathe, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 1608 days.

(21) Appl. No.: 10/294,963

(22) Filed: Nov. 14, 2002

(65) Prior Publication Data

US 2004/0098286 A1 May 20, 2004

(51) Int. Cl.
*G06Q 10/00* (2006.01)
*G06Q 50/00* (2006.01)
*G06Q 40/00* (2006.01)

(52) U.S. Cl. ..................... 705/2; 705/3; 705/4
(58) Field of Classification Search ............. 705/2–4
See application file for complete search history.

(56) References Cited

U.S. PATENT DOCUMENTS

| | | | |
|---|---|---|---|
| 4,857,716 A | 8/1989 | Gombrich | |
| 5,153,827 A | 10/1992 | Coutre | |
| 5,317,506 A | 5/1994 | Coutre | |
| 5,594,786 A | 1/1997 | Chaco | |
| 5,682,728 A | 11/1997 | DeBusk | |
| 5,737,539 A * | 4/1998 | Edelson et al. | 705/3 |
| 5,748,907 A * | 5/1998 | Crane | 705/2 |
| 5,781,442 A | 7/1998 | Engleson | |
| 5,991,728 A | 11/1999 | DeBusk | |
| 6,085,493 A | 7/2000 | DeBusk | |
| 6,139,495 A * | 10/2000 | De La Huerga | 600/300 |
| 6,151,582 A | 11/2000 | Huang | |
| 6,519,569 B1 | 2/2003 | White | |
| 6,671,563 B1 | 12/2003 | Engelson | |
| 6,731,989 B2 | 5/2004 | Engleson | |
| 6,790,198 B1 | 9/2004 | White | |
| 6,892,512 B2 * | 5/2005 | Rice et al. | 53/445 |
| 6,915,170 B2 | 7/2005 | Engleson | |
| 6,985,870 B2 | 1/2006 | Martucci | |

(Continued)

FOREIGN PATENT DOCUMENTS

WO    WO9606944 A1    7/1996

OTHER PUBLICATIONS

Business Wire, "Cerner Annoiunces Strong Penetration of the Community-Based Healthcare Marketplace." Nov. 2000.*

(Continued)

*Primary Examiner* — Neal Sereboff
(74) *Attorney, Agent, or Firm* — Shook, Hardy & Bacon L.L.P.

(57) ABSTRACT

A method in a computer system for preparing for a clinical event is provided. In a preferred embodiment, the method includes the steps of identifying a preference card associated with the clinical event, the preference card including a list of predefined clinical item values, accessing at least one patient-specific demographic value; determining whether at least one of the predefined clinical item values is incompatible with at least one patient-specific demographic value, and updating the preference card if at least one of the predefined clinical item values is incompatible with at least one patient-specific demographic value.

77 Claims, 7 Drawing Sheets

U.S. PATENT DOCUMENTS

| | | |
|---|---|---|
| 7,096,072 B2 | 8/2006 | Engleson |
| 7,103,419 B2 | 9/2006 | Engleson |
| 7,107,106 B2 | 9/2006 | Engleson |
| 7,117,041 B2 | 10/2006 | Engleson |
| 2001/0001144 A1* | 5/2001 | Kapp ................................. 705/3 |
| 2002/0007290 A1 | 1/2002 | Gottlieb |
| 2002/0032582 A1* | 3/2002 | Feeney et al. ..................... 705/2 |
| 2002/0042725 A1* | 4/2002 | Mayaud ............................ 705/2 |
| 2002/0077850 A1 | 6/2002 | McMenimen |
| 2002/0082866 A1 | 6/2002 | Ladouceur |
| 2002/0099275 A1* | 7/2002 | Schmidt et al. ............... 600/300 |
| 2002/0116372 A1* | 8/2002 | Ladouceur et al. ................ 707/3 |
| 2002/0188179 A1* | 12/2002 | Bulat ............................ 600/300 |
| 2002/0188469 A1 | 12/2002 | Shalmi |
| 2003/0023500 A1 | 1/2003 | Boles |
| 2003/0055685 A1 | 3/2003 | Cobb |
| 2003/0069774 A1 | 4/2003 | Hoffman |
| 2003/0132249 A1 | 7/2003 | Romano |
| 2003/0139701 A1 | 7/2003 | White |
| 2004/0044546 A1 | 3/2004 | Moore |
| 2004/0098286 A1 | 5/2004 | Zimmerman |
| 2004/0128163 A1* | 7/2004 | Goodman et al. ................. 705/2 |
| 2004/0138921 A1* | 7/2004 | Broussard et al. ................ 705/2 |
| 2005/0027563 A1 | 2/2005 | Fackler |
| 2005/0107914 A1 | 5/2005 | Engleson |
| 2005/0108140 A1 | 5/2005 | Motte |
| 2007/0162265 A1* | 7/2007 | Hall .................................. 703/3 |

OTHER PUBLICATIONS

HighBeam Research, "U.S. Department of Defense Picks Cerner Solution to Implement DOD-Wide Operating Room Management Application" Jan. 2000.*
Cerner Annual Report, 1999.*
Funding Universe, "Cerner Corporation—Company History" as downloaded Nov. 2010.*
Cerner Web Page, "Care Products" Aug. 2001.*
Office Action for U.S. Appl. No. 10/750,217 dated Feb. 22, 2008.
Office Action for U.S. Appl. No. 10/750,216 dated Sep. 6, 2007.
Office Action for U.S. Appl. No. 10/750,221 dated Jan. 23, 2008.
Office Action for U.S. Appl. No. 10/750,210 dated Apr. 29, 2008.
Office Action for U.S. Appl. No. 11/351,576 dated Feb. 10, 2006.
Office Action for U.S. Appl. No. 11/351,575 dated Jan. 14, 2008.
Office Action for U.S. Appl. No. 11/351,460 dated Feb. 10, 2006.

* cited by examiner

AUTOMATED SYSTEM FOR MANAGING THE SELECTION OF CLINICAL ITEMS AND DOCUMENTATION FOR A CLINICAL EVENT

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates to a computer system and, more particularly, to a computer system for automatically selecting clinical items and documentation for a clinical event based on patient-specific information.

BACKGROUND OF THE INVENTION

In a healthcare environment, a number of clinical items are required to treat a patient during a clinical event or encounter. For example, a variety of medications, instruments, supplies and pieces of equipment are required to perform a surgical procedure. While certain types of clinical items are required by all physicians for each kind of procedure, most physicians have preferences as to the specific configuration, brand, model or quantity of clinical items used to perform each type of procedure. Additionally, the preferred clinical items may include optional items and incidental items that other physicians do not use when performing the same operation.

Typically, each physician develops a preference card containing a list of clinical items that the particular physician prefers to use for a particular procedure. This list of clinical items is referred to as a pick list. Each preference card also includes documentation relevant to preparing for the procedure and documenting the events that occur before, during and after the procedure. These preference cards are stored either physically or electronically at the hospital at which the procedure will be performed. In order to assemble the clinical items for a procedure, the appropriate preference card is first selected. Then, the clinical items appearing on the pick list are removed from the hospital's inventory and placed either directly in the operating room or on a surgical cart that is subsequently located in the operating room.

While this process provides the physician with the clinical items identified by the preference card, the process does not account for variations in the pick list attributable to the particular patient at the center of the clinical event. For instance, in most cases, the pick list of the preference card includes a number of items that are not needed for the particular patient since the pick list is built for patients of all different ages, sizes and types. In some cases, the patient may be allergic to a particular item included on the preference card. It is typically the responsibility of the hospital personnel assembling the clinical items to remove the inappropriate clinical item from the printed pick list from which the hospital personnel is operating.

This process is deficient for a number of reasons. By allowing clinically inappropriate items into the operating room (or other healthcare setting), an inappropriate item may inadvertently or unknowingly contact the patient and adverse or atypical effects may follow. Likewise, the changes to the documentation portion of the procedure must be made manually, and similar shortcomings are encountered. Further, larger inventories are required at the clinical facility, and additional opportunities for mistakes are created due to the assembly of unnecessary items. For these and a number of reasons, the preference card is poorly suited to manage the inventory of the hospital, charge the patient for items used during the procedure or otherwise manage the administration processes of the hospital.

Modern healthcare information systems have failed to solve these problems. In at least one system, a warning may be provided to the user of the information system that a clinical item on the pick list may be harmful to some patients. However, this system requires the user of the computer system to receive the notification and to adjust the pick list. Additionally, these changes are entered by the user manually, and the corrected list is not distributed to all of the supply rooms around the hospital. Thus, the system suffers from the same drawbacks as conventional methods of managing preference cards. Accordingly, there is a need for an effective system and method for automatically selecting the clinical items and documentation for a clinical event based on patient-specific information to improve patient safety. A need also exists for a system and method for completely and accurately identifying the clinical items used at the point of care (or admission) and initiating administrative and clinical processes based on the complete and accurate list of items used at the point of care. Still another need is for a system and method for managing items of a pick list to reduce liability and produce efficiencies not previously realized. There is yet another need for a system and method that accesses information regarding newly discovered knowledge about the appropriateness of a clinical item for a person, and utilizes the knowledge by applying rules to safely and effectively treat a patient.

SUMMARY OF THE INVENTION

Generally described, a method in a computer system for preparing for a clinical event is provided. The method includes the step of identifying a preference card associated with the clinical event. The preference card includes a list of predefined clinical item values. The method also includes the steps of accessing at least one patient-specific demographic value, determining whether at least one of the predefined clinical item values is incompatible with at least one patient-specific demographic value, and updating the preference card if at least one of the predefined clinical item values is incompatible with at least one patient-specific demographic value.

In another aspect of the invention, another method in a computer system for preparing for a clinical event associated with a patient is provided. The method includes the steps of receiving scheduling information and identifying a preference card associated with the scheduling information. The preference card includes a list of predefined values. The method also includes the steps of accessing a plurality of patient-specific values, determining whether at least one of the predefined values is incompatible with at least one patient-specific value, and updating the preference card if at least one of the predefined values is incompatible with at least one patient-specific value.

In still another aspect of the invention, another method in a computer system for preparing for a clinical event associated with a patient is provided. The method includes the steps of receiving scheduling information and identifying a first preference card associated with the scheduling information. The preference card includes a list of predefined values. The method also includes the steps of accessing a plurality of patient-specific demographic values, determining whether at least one of the predefined values is incompatible with at least one demographic patient-specific value, and updating the preference card if at least one of the predefined values is incompatible with at least one patient-specific demographic value.

Additional advantages and novel features of the invention will be set forth in part in a description which follows, and in part will become apparent to those skilled in the art upon examination of the following, or may be learned by practice of the invention.

BRIEF DESCRIPTION OF THE DRAWINGS

The present invention is described in detail below with reference to the attached drawing figures, wherein.

DETAILED DESCRIPTION

Figure 1:
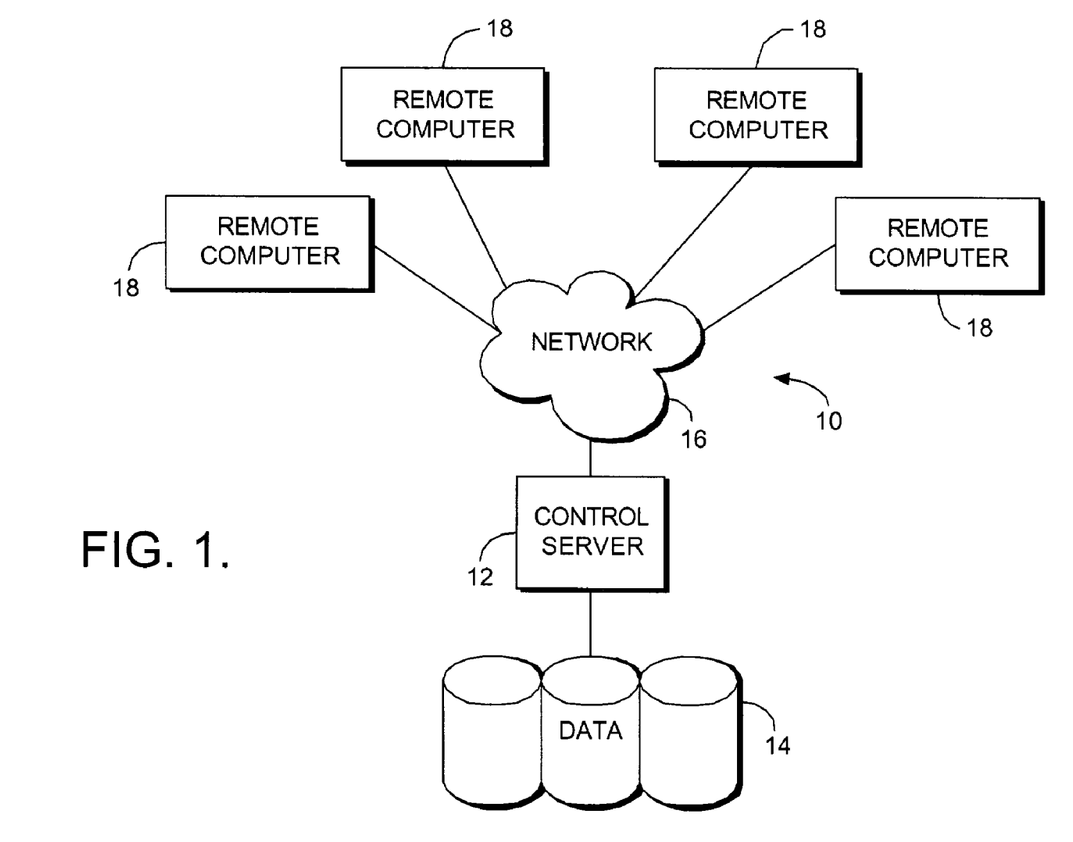
FIG. 1 is a schematic diagram of a suitable computing system environment for use in implementing the present invention.

The present invention provides a method and system for managing the selection of clinical items and documentation for a clinical event. FIG. 1 illustrates an example of a suitable computing system environment 10 on which the invention may be implemented. The computing system environment 10 is only one example of a suitable computing environment and is not intended to suggest any limitation as to the scope of use or functionality of the invention. Neither should the computing environment 10 be interpreted as having any dependency or requirement relating to any one or combination of components illustrated in the exemplary environment 10.

The invention is operational with numerous other general purpose or special purpose computing system environments or configurations. Examples of well-known computing systems, environments, and/or configurations that may be suitable for use with the invention include, but are not limited to, personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components and data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary system for implementing the invention includes a general purpose computing device in the form of server 12. Components of server 12 may include, but are not limited to, a processing unit, internal system memory, and a suitable system bus for coupling various system components, including a database cluster 14 to the control server 12. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 12 typically includes therein or has access to a variety of computer readable media, for instance, database cluster 14. Computer readable media can be any available media that can be accessed by server 12, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 12. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 14, discussed above and illustrated in FIG. 1, provide storage of computer readable instructions, data structures, program modules, and other data for server 12. Server 12 may operate in a computer network 16 using logical connections to one or more remote computers 18. Remote computers 18 can be located at a variety of locations in a medical or clinical laboratory environment, for example, but not limited to, hospitals, other inpatient settings, testing labs, medical billing and financial offices, and hospital administration. Each remote computer 18 may be a personal computer, server, router, a network PC, a peer device or other common network node, and may include some or all of the elements described above relative to server 12. Computer network 16 may be a local area network (LAN) and/or a wide area network (WAN), but may also include other networks. Such networking environments are commonplace in offices, enterprise-wide computer networks, intranets and the Internet. When utilized in a WAN networking environment, server 12 may include a modem or other means for establishing communications over the WAN, such as the Internet. In a networked environment, program modules or portions thereof may be stored in server 12, or database cluster 14, or on any of the remote computers 18. For example, and not limitation, various application programs may reside on the memory associated with any one or all of remote computers 18. It will be appreciated that the network connections shown are exemplary and other means of establishing a communications link between the computers may be used.

By way of example, a user may enter commands and information into server 12 or convey the commands and information to the server 12 via remote computers 18 through input devices, such as keyboards or pointing devices, commonly referred to as a mouse, trackball, or touch pad. Other input devices may include accepting data from an interface or logic system, microphone, satellite dish, scanner, or the like. Server 12 and/or remote computers 18 may have any sort of display device, for instance, a monitor. In addition to a monitor, server 12 and/or computers 18 may also include other peripheral output devices, such as speakers and printers.

Although many other internal components of server 12 and computers 18 are not shown, those of ordinary skill in the art will appreciate that such components and their interconnection are well known. Accordingly, additional details concerning the internal construction of server 12 and computers 18 need not be disclosed in connection with the present invention.

The method and system of the present invention includes the steps of accessing at least one patient-specific demographic value, determining whether at least one of the predefined clinical item values is incompatible with at least one patient-specific demographic value, and updating the preference card if at least one of the predefined clinical item values is incompatible with at least one patient-specific demographic value. Although the method and system are described as being implemented in a WINDOWS operating system operating in conjunction with a comprehensive healthcare network, one skilled in the art would recognize that the method and system can be implemented on any system supporting the receipt and processing of scheduling information or the like.

The system and method are described by reference to surgical settings. However, the invention is contemplated for use in any healthcare environment requiring a number of clinical items or clinical documentation. For instance, the system and method may be employed in other departments of the hospital such as cardiology and radiology departments, outpatient settings, doctor's offices, home health and other environments.

Figure 2A:
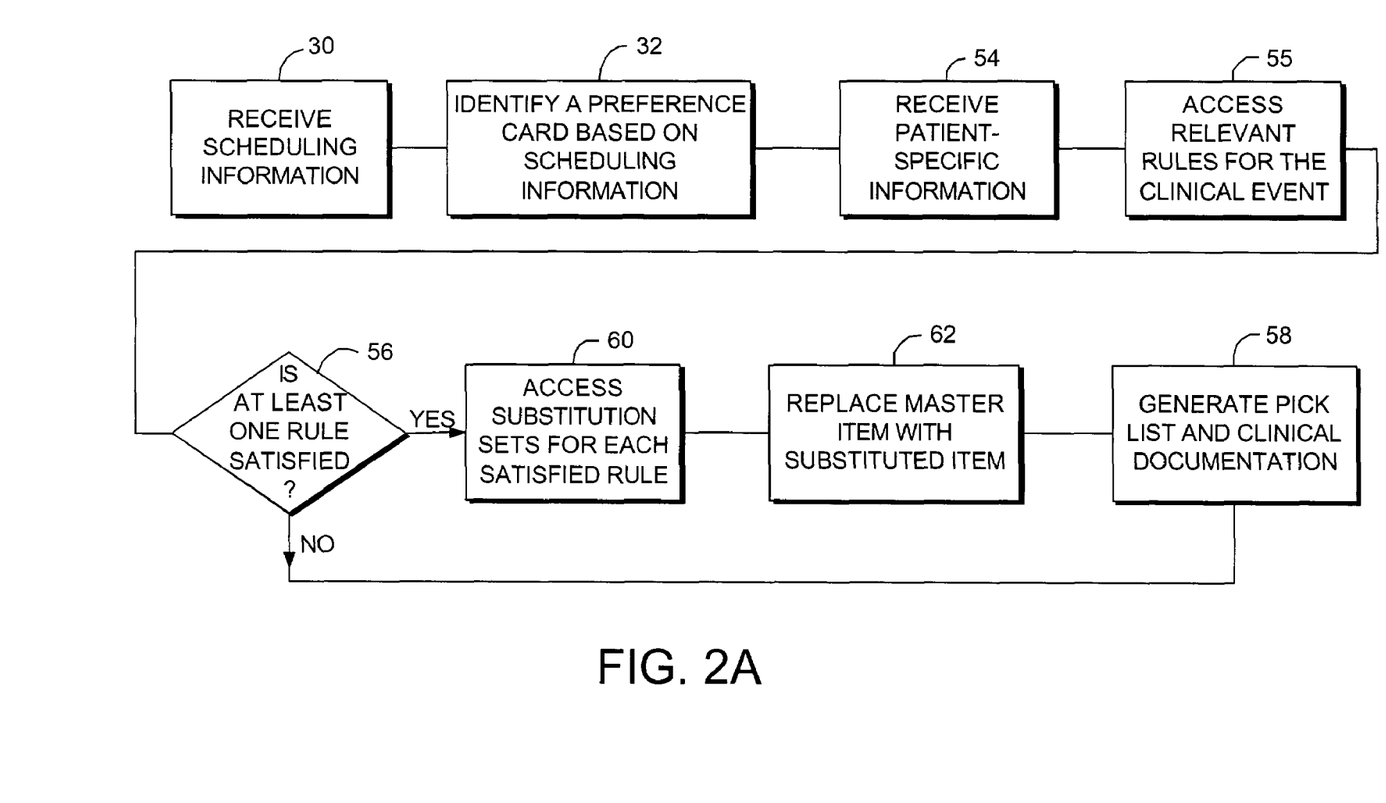
FIG. 2A-B is a flow diagram illustrating the overall method for managing the selection of clinical items and documentation for a clinical event.

With reference to FIG. 2, in the preferred embodiment of the present invention, a system and method for selecting clinical items and documentation for a clinical procedure is shown. At step 30, scheduling information is received. Scheduling information as used herein includes information identifying the clinician (or caregiver), the type of clinical event, or the specialty of the clinician or the patient location. As used herein, a clinician includes but is not limited to, the treating physician, specialist such as surgeons, radiologists and cardiologists, emergency medical technicians, physician's assistants, nurse practioners, nurses, nurses's aides, dieticians and the like. Clinical events include, but are not limited to non-invasive procedures, surgical procedures, examinations, evaluations, testing and the like.

As known in the art, within an integrated healthcare information system, the scheduling information may be received by a remote computer system at an administrative location and populated into the clinical application prior to the preparation for the procedure. Alternatively, the scheduling information may be received directly in the clinical application.

Figure 3:
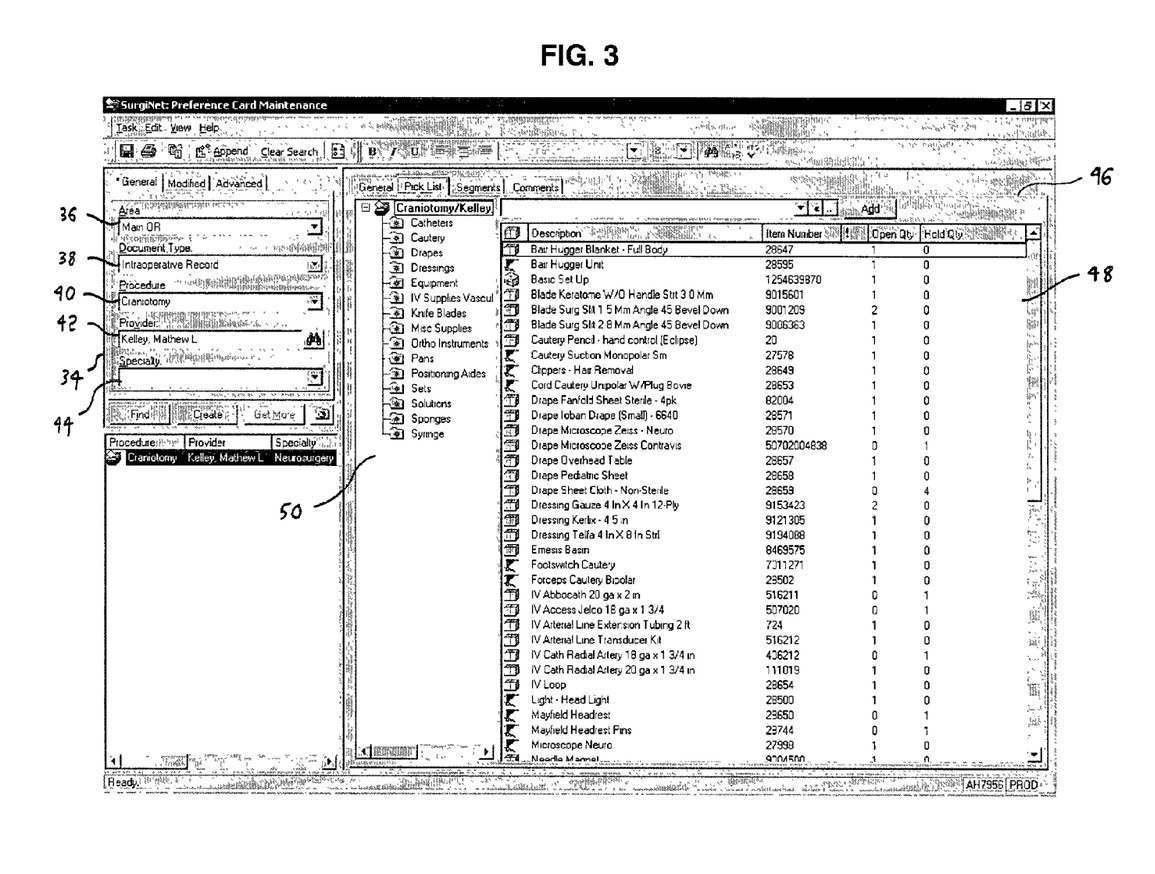
FIG. 3 is a representative graphical user interface displaying a pick list of a preference card.

Next, at step 32, the system identifies a preference card based on the scheduling information received at step 30. As known in the art, preference cards are most commonly used in connection with surgical operations to provide the clinician and the hospital staff with the information required to perform the surgical procedure. As shown in FIG. 3, an exemplary view of a first graphical user interface of a preference card is shown for purposes of explaining the present invention. The exemplary preference card includes a first portion 34 for displaying the scheduling information discussed above. Specifically, the first portion 34 includes a first field 36 indicating the area at which the event will occur, a second field 38 indicative of the document type that will be used to perform and document the procedure (i.e. pre-operative, intraoperative or post-operative), a third field 40 indicating the type of clinical event to occur, a fourth field 42 identifying the clinician responsible for the clinical event and a fifth field 44 indicating the specialty associated with the procedure or event.

A second portion 46 of the preference card includes the substantive information required to perform the procedure. Namely, as shown in FIG. 3, each preference card includes a pick list 48 having a list of clinical items that may be needed for the procedure. As used herein, a clinical item includes but is not limited to a piece of medical equipment, an instrument, a medication, a supply, a dressing, a resource or any of a number of other items used as part of a clinical event. Preferably, for each clinical item on the pick list, a description of the item, an item number and "open" and "hold" quantities are displayed on the pick list. The description of the item is the common name of the item and the item number is a unique identifier associated with the description. The "open" quantity indicates the number of items that should be opened and prepared for use prior to being placed on the surgical cart or placed directly in the operating room (or other clinical setting). The "hold" quantity indicates the number of items that should be placed on the cart or directly in the operating room. "Hold" items are not opened prior to the clinical event. The use of these items is oftentimes dependent on the tasks that transpire during the clinical event. For instance, additional items may be needed if the patient reacts differently from the typical patient during the steps of the clinical event.

As shown in a preferred embodiment of FIG. 3, the items on pick list 48 may be divided into a number of categories by selecting from the list of categories in a menu 50. For instance, by selecting "medication" in menu 50, only the medications in the comprehensive pick list are displayed to the user of the system.

In addition to the pick list of the preference card, the preference card includes documentation information needed before, during and after the clinical event. Specifically, a number of documentation segments are included on the preference card to assist the clinicians in performing the clinical event and document the steps during the clinical event. Preferably, each preference card includes documentation segments for case attendance, case times, general case data and surgical procedure. As known in the art, additional documentation segments may be included in the preference card to assist in performing and documenting the procedure.

Figure 4:
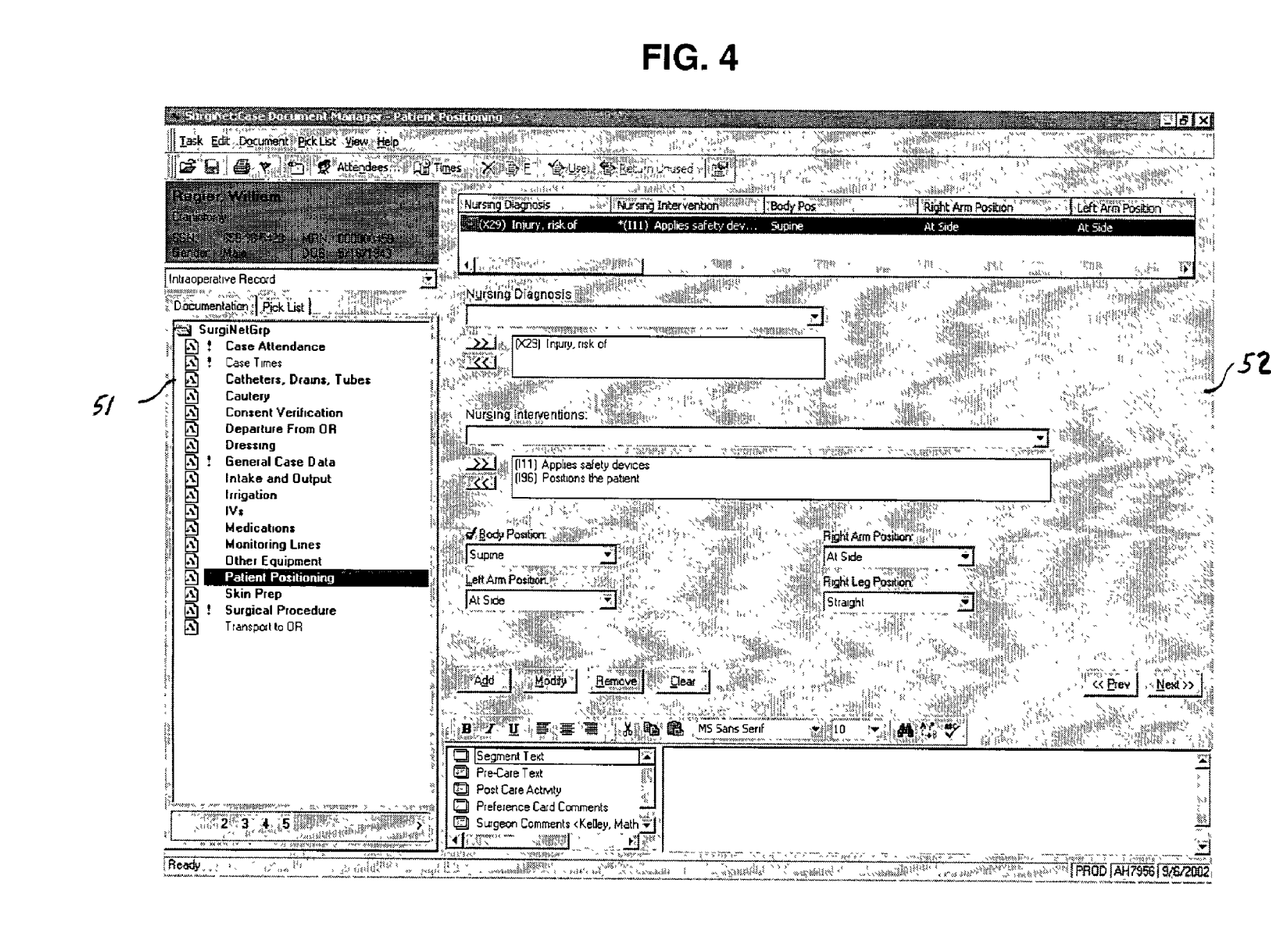
FIG. 4 is a representative graphical user interface displaying documentation segments of a preference card.

With reference to FIG. 4, a second view of the exemplary preference card of FIG. 3 illustrates one of a number of documentation segments for a clinical event. In a first portion 51 of the user interface, a list of documentation segments is displayed in the user interface. In FIG. 4, the selected documentation segment if for patient positioning during the clinical event. For the selected segment, a list of the documentation values is shown as part of a template at a second portion 52. Specifically, as shown in FIG. 4, the values associated with nursing diagnosis, nursing intervention, body position, left arm position and right arm position are displayed in second portion 52 to assist the clinician conducting the clinical event.

Preferably, the preference cards are stored in a relational database wherein the values of each preference card are stored in a series of tables. As known to those of skill in the art, one of any number of data models may be employed to store information relative to the preference cards. Each clinical item has a clinical item value associated with the item. Preferably, each clinical item value is an identification number unique to the clinical item. The pick list table in the database for each preference card includes a table of the clinical item identification values. Likewise, documentation values are stored in a number of tables associated with each type of documentation segment.

With reference back to FIG. 2, at step 32, one of a number of preference cards is identified by selecting the card associated with the scheduling information from a database contain the preference cards. Typically, a preference card is stored by reference to the clinician that will perform the clinical event and the type of clinical event. As such, the system searches the database based on the clinician identification and procedure type information received at step 30 and identifies the appropriate preference card. In other cases, the preference card may be selected based on additional scheduling information including the area at which the clinical event will occur, type of documentation required for the clinical event or the specialty associated with the clinical event.

Next, at step 54, the system receives patient-specific information. Preferably, patient-specific information includes a number of patient-specific values associated with one of a number of patient-specific data types in the electronic medical record or other storage media. The patient-specific values are either demographic or non-demographic data types. Demographic information as used herein shall include values indicative of the gender, age, weight or height of the patient, known allergies of the patient, genetic information, and information about particular problems associated with the patient. Non-demographic information as used herein shall include values indicative of appointment location, encounter type, event detail, order detail, orderable, or surgeon group, specialty group or procedure group to which the patient is assigned.

The patient-specific information may be received in any of a number of ways. Preferably, in an integrated healthcare information system, the patient-specific information is received by querying a database for an electronic medical record (EMR) containing the patient-specific information. Also, the receipt of patient-specific information into the system of the present invention may precede steps 30 and 32. Alternatively, the patient-specific information may be received simultaneously with the scheduling information at step 30.

Next, the system initiates the review of the clinical items on the pick list of the preference card to determine if one or more or the clinical items are incompatible with the patient-specific information. Specifically, at step 55, the system accesses a number of clinical rules. In a preferred embodiment, each rule identifies whether any of the patient-specific values received at step 54 are incompatible with the clinical items on the pick list of the preference card. As discussed above, the patient-specific values are typically stored within data types (or categories) in an electronic medical record. Preferably, each rule compares a patient-specific value of a particular data type against a predefined test value. For example, when the preference card relates to a surgical case, the demographic values in the patient record are typically stored in one of the following data value types: allergies, genetic makeup, age, birth date, gender, height, weight, and presenting problem. The non-demographic values are typically stored in one of the following data value types: appointment location, encounter type, event detail, order detail, orderable, surgeon group, surgeon specialty group and surgical procedure group. As used herein, encounter type relates to whether the encounter is inpatient or outpatient. Event detail describes any of a number of details associated with the event such as whether the event was pre-certified or when the event was scheduled relative to another event. Order detail describes any detail associated with a clinical order such as the type of anesthetic to use, the side of the body on which an order should be executed, and the like.

The clinical rule compares a pre-defined test value to a patient-specific value within a specific data value type. The comparison of the pre-defined test value against the patient-specific value may use a variety of logical operations. For instance, the rule may require that the patient-specific value for the identified data value type is the same as the test value, is greater than the test value or is less than the test value. Additionally, a number of rules may be employed to determine if an incompatibility exists. For instance, patient-specific values could be aggregated to determine if a rule is satisfied. Alternatively, Boolean logic may be used to structure one or more rules.

If none of the rules are satisfied, the pick list and clinical event documentation are generated at step 58. If at least one rule or rule set is satisfied, substitution sets are accessed at step 60. Each rule has an associated substitution set including a master item and a substituted item. The master item is a clinical item, segment of documentation or default documentation. As used herein, default documentation is the collection of the pick list and documentation segments. When the rule associated with the master item is satisfied, the substitute item is replaced on the preference card. The substitute item is another clinical item, segment of documentation or default documentation. Preferably, if the master item is a clinical item, then the substituted item or items is also a clinical item. In other cases, the master item may be removed without the addition of a replacement item. Likewise, if the master item is a segment of documentation or default documentation, the substitute item is either a segment of documentation or default documentation, respectively. Once the substitutions are made at step 62, the pick list and clinical documentation are generated at step 58.

Figure 2B:
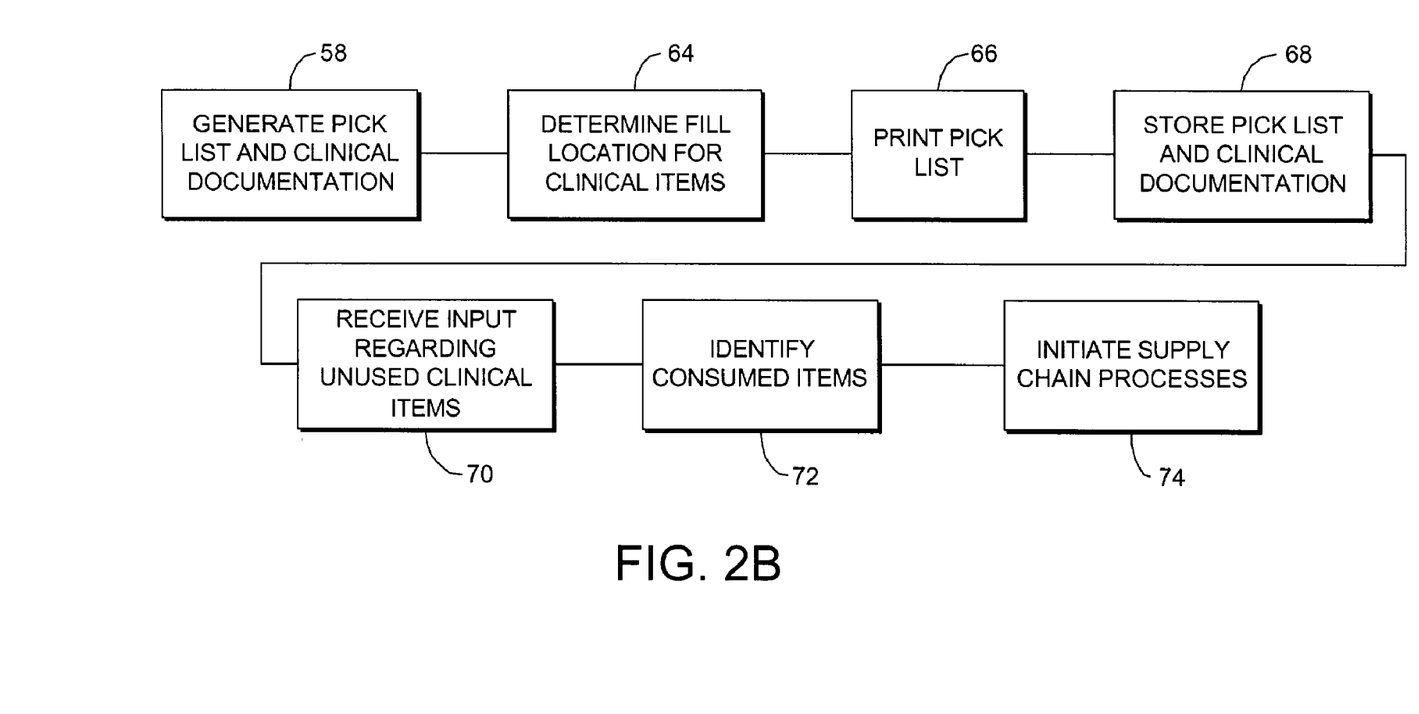

With reference to FIG. 2B, once the pick list and clinical documentation of the preference card are generated at step 58, the fill locations for the clinical items are determined at step 64. As known in the art, the fill location is typically determined by the location at which the clinical event will occur. After the fill location is determined, the pick list is printed at step 66. In many cases, the pick list will be routed and printed at a remote storeroom (or other location) to be filled. The printed pick list is used to assemble the clinical items required to prepare for the clinical event. Alternatively, the pick list may be displayed on a personal computer or a wireless device rather than being printed. At step 68, the pick list and clinical documentation of the preference card are stored. Preferably, the documentation is stored in the patient's electronic medical record.

Figure 5:
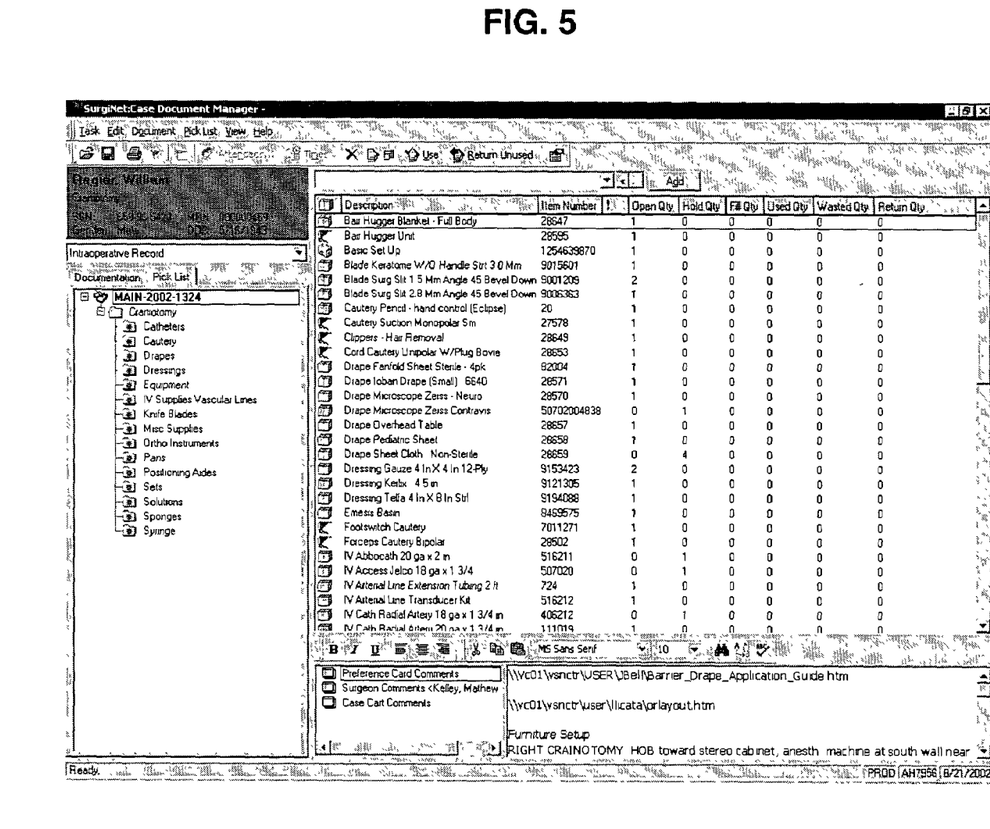
FIG. 5 is a representative graphical user interface displaying a pick list of a preference card for documenting the consumption of clinical items.

With reference to FIG. 5, another view of the preference card is shown. In this view, the pick list displayed in second portion 52 of the preference card contains a category entitled "FILL" in addition to the categories for "OPEN QTY" and "HOLD QTY". As the user assembles the items on the pick list, the user may input the quantity of items placed on the cart or in the appropriate location into the system. This quantity is stored in the system and represented on the graphical user interface of FIG. 5. The input may be received directly from the user, through a barcode scanner or other input.

Once the clinical event occurs, the unused items are returned to the appropriate storage facility. At step 70, input is received to identify those clinical items that appeared on the pick list for the clinical event but were unused. With reference back to FIG. 5, second portion 52 of the pick list displays categories for displaying the quantity of each item that is used during the event, wasted during the event and returned to the inventory after the event are displayed. Similar to the filling process, the input may be directly from the user, through a barcode scanner or other input. Once the input is received, the system can identify the items consumed during the clinical procedure at step 72. In some cases, user input of each item used, wasted and consumed will directly lead to the identification of consumed items. In other instances, the returned quantify may be determined from decrementing the used items (if single use) and wasted items from items filled on the cart. Once this is complete, at step 74, a number of supply chain processes may be initiated by using this information. By way of example and not limitation, this information may be used to charge patient, decrement inventory, order replenishments and any of a number of other known supply chain processes.

In operation, by way of a number of examples in which a clinical item or documentation segment is incompatible with a patient-specific value, a number of processes are described herein.

In the first example, the clinical event is an exploratory laparotomy, and the patient is an adult weighing 155 pounds and having an allergy to latex. With reference to FIG. 2A, a user schedules the clinical event for the patient at step 30. The scheduling information includes the clinician's name and an identification of the procedure. Next, at step 32, the system identifies the appropriate preference card based on the scheduling information received at step 30.

By way of example, the preference card identified at step 32 includes the following pick list:

| Item Description | Open Qty | Hold Qty |
| --- | --- | --- |
| Basic Setup | 1 | 0 |
| Basic Setup-Latex Free | 0 | 1 |
| Blade #20 | 1 | 0 |
| Blade #10 | 2 | 0 |
| Blade #15 | 1 | 1 |
| Cautery Cleaner | 2 | 0 |
| Cautery Pencil - Hand Control (Eclipse) | 2 | 0 |
| Drape Steri-Drape - 1050 | 1 | 0 |
| Dressing Steristrip 0.25 In x 4 In | 1 | 0 |
| Drape Ioban Steri-Drape - 6640 | 1 | 0 |
| Dressing Telfa 4 In x 8 In Strl | 1 | 0 |
| Glove Microtouch Sz 6.5 | 1 | 0 |
| Glove Nitra-Touch Latex-Free Sz 6.5 | 0 | 1 |
| Light Handle Set (3) | 1 | 0 |
| Needle Magnet | 1 | 0 |
| Pack Laparotomy/Abdominal Adult | 1 | 0 |
| Pack Laparotomy/Abdominal Adult - Latex Free | 0 | 1 |
| Pack Laparotomy/Abdominal Pediatric | 0 | 1 |
| Pad Grounding Cautery Adult | 1 | 0 |

-continued

| Item Description | Open Qty | Hold Qty |
| --- | --- | --- |
| Pad Grounding Cautery Pediatric | 0 | 1 |
| Set Extra Long Instrument | 0 | 1 |
| Set Laparatomy | 1 | 0 |
| Set Pediatric | 0 | 1 |
| Solution Benzoin Ampule | 1 | 0 |
| Solution Dura-Prep Sgl-Use | 1 | 1 |
| Sponge 4 x 4 Raytec 16 Ply | 0 | 2 |
| Sponge Lap 4 In x 18 In Prewshd Strl | 4 | 0 |
| Suture Prolene 1-0 CT-1 | 3 | 0 |
| Suture Vicryl 2.0 SH | 0 | 2 |
| Suture Vicryl 0 CT-2 | 2 | 0 |
| Suture Vicryl 0 SH | 0 | 3 |
| Syringe Asepto | 2 | 0 |
| Tegaderm - 4 x 4 ¾ | 1 | 0 |
| Tray Cath Foley w/Bag 16 Fr 5 cc | 1 | 0 |
| Tray Cath Foley w/Bag 6 Fr 5 cc | 0 | 1 |
| Tube Culturette Aerobic | 1 | 0 |
| Tube Culturette Anaerobic | 1 | 0 |

At this point, the pick list of the selected preference card includes fifty-three clinical items since the default preference card includes items for all different types of patients and all different circumstances.

Next, at step 55, the system accesses the rules relevant to an exploratory laparotomy. A number of rules are accessed at this step. In this example, a first rule has a pre-defined test value of "LATEX" and is satisfied if the patient-specific information includes a patient-specific value of "LATEX" for the data value type associated with an allergy. In another instance, a second rule is satisfied if a patient is a child or small adult. Technically, the rule is satisfied if the patient-specific information includes a value for weight less than a pre-defined test value of 200 pounds and more than a pre-defined test value of 120 pounds.

At step 56, the system determines if at least one rule accessed at step 54 is satisfied. In this example, the electronic medical record includes a patient-specific value indicating an allergy to latex, and the rule is satisfied. Since the rule is satisfied, the system accesses the substitution set for the rule at step 60. For this rule, the substitution set removes all master items rather than replacing them with a substituted item. The substitution set for this rule would be structured as follows:

| Master Item | Substituted Item |
| --- | --- |
| Basic Setup | Null value |
| Glove Microtouch Sz 6.5 | Null value |
| Pack Laparotomy/Abdominal Adult | Null value |

The rule associated with the patient's weight is also satisfied in this example. When applied, the substitution set for this rule removes inappropriate clinical items based on the patient's size. The substitution set applied when this rule is satisfied is as follows:

| Master Item | Substituted Item |
| --- | --- |
| Pad Grounding Cautery Pediatric | Null value |
| Set Extra Long Instrument | Null value |
| Set Pediatric | Null value |
| Sponge 4 x 4 Raytex 16 Ply | Null value |
| Suture Vicryl 0 2.0 SH | Null value |

Next, at step 62, the substituted items replace the master items for both clinical rules. In this example, the master items are removed from the preference card. Next, at step 58, the pick list and documentation of the preference card are generated by the system. The pick list at this point contains the following clinical items:

| Item Description | Open Qty | Hold Qty |
|---|---|---|
| Basic Setup - Latex Free | 0 | 1 |
| Blade #20 | 1 | 0 |
| Blade #10 | 2 | 0 |
| Blade #15 | 1 | 1 |
| Cautery Cleaner | 2 | 0 |
| Cautery Pencil - Hand Control (Eclipse) | 2 | 0 |
| Drape Ioban Drape - 6650EZ | 1 | 0 |
| Dressing Steristrip 0.25 In × 4 In | 1 | 0 |
| Drape Ioban Steri-Drape - 6640 | 1 | 0 |
| Dressing Telfa 4 In × 8 In Strl | 1 | 0 |
| Glove Nitra-Touch Latex-Free Sz 6.5 | 0 | 1 |
| Light Handle Set (3) | 1 | 0 |
| Needle Magnet | 1 | 0 |
| Pack Laparotomy/Abdominal Adult - Latex Free | 0 | 1 |
| Pad Grounding Cautery Adult | 1 | 0 |
| Set Laparatomy | 1 | 0 |
| Solution Benzoin Ampule | 1 | 0 |
| Solution Dura-Prep Sgl-Use | 1 | 1 |
| Sponge Lap 4 In × 18 In Prewshd Strl | 4 | 0 |
| Suture Prolene 1-0 CT-1 | 3 | 0 |
| Suture Vicryl 0 CT-2 | 2 | 0 |
| Syringe Asepto | 2 | 0 |
| Tegaderm - 4 × 4 ¾ | 1 | 0 |
| Tray Cath Foley w/Bag 16 Fr 5 cc | 1 | 0 |
| Tube Culturette Aerobic | 1 | 0 |
| Tube Culturette Anaerobic | 1 | 0 |

With the inappropriate items removed from the preference card, only thirty-seven clinical items are required to be placed in the surgical area. With reference to FIG. 2B, once the pick list is generated, the system determines the fill locations for the clinical items at step 64 and the pick list is printed at step 66 at a storeroom located in proximity to the operating room. At step 68, the pick list and documentation of the preference card are stored. Once the procedure is complete, a member of the hospital staff returns any unused items to the storeroom and provides that input to the system at step 70. The system determines the number of items consumed at step 72 by comparing the returned items to the number of the items on the default preference card or the number of items actually filled based on user input received prior to storing the pick list at step 68. In this example, the default preference card included all of the clinical items needed to perform the exploratory laparotomy for all variations of patients. Once the rules are applied, the unnecessary and clinically inappropriate items are removed.

Alternatively, the default preference card identified at step 32 may include clinical items that are replaced if a rule is satisfied and a substitution set applied. For instance, the preference card may contain the following clinical items for an exploratory laparatomy:

| Item Description | Open Qty | Hold Qty |
|---|---|---|
| Basic Setup | 1 | 0 |
| Blade #20 | 1 | 0 |
| Blade #10 | 2 | 0 |
| Blade #15 | 1 | 1 |
| Cautery Cleaner | 2 | 0 |
| Cautery Pencil - Hand Control (Eclipse) | 2 | 0 |
| Drape Ioban Drape - 6650EZ | 1 | 0 |
| Dressing Steristrip 0.25 In × 4 In | 1 | 0 |
| Drape Ioban Steri-Drape - 6640 | 1 | 0 |
| Dressing Telfa 4 In × 8 In Strl | 1 | 0 |
| Glove Microtouch Sz 6.5 | 1 | 0 |
| Light Handle Set (3) | 1 | 0 |
| Needle Magnet | 1 | 0 |
| Pack Laparotomy/Abdominal Adult | 1 | 0 |
| Pad Grounding Cautery Adult | 1 | 0 |
| Set Laparatomy | 1 | 0 |
| Solution Benzoin Ampule | 1 | 0 |
| Solution Dura-Prep Sgl-Use | 1 | 1 |
| Sponge Lap 4 In × 18 In Prewshd Strl | 4 | 0 |
| Suture Prolene 1-0 CT-1 | 3 | 0 |
| Suture Vicryl 0 CT-2 | 2 | 0 |
| Syringe Asepto | 2 | 0 |
| Tegaderm - 4 × 4 ¾ | 1 | 0 |
| Tray Cath Foley w/Bag 16 Fr 5 cc | 1 | 0 |
| Tube Culturette Aerobic | 1 | 0 |
| Tube Culturette Anaerobic | 1 | 0 |

With reference to the patient described above, the rule relating to an allergy is satisfied, and the substitution set is as follows:

| Master Item | Substituted Item |
|---|---|
| Basic Setup | Basic Setup - Latex Free |
| Glove Microtouch Sz 6.5 | Glove Nitra-Touch Latex-Free Sz 6.5 |
| Pack Laparotomy/Abdominal Adult | Pack Laparotomy/Abdominal Adult-Latex Free |

Once the substitution set is applied, the preference card would contain the following clinical items for an exploratory laparatomy:

| Item Description | Open Qty | Hold Qty |
|---|---|---|
| Basic Setup - Latex Free | 1 | 0 |
| Blade #20 | 1 | 0 |
| Blade #10 | 2 | 0 |
| Blade #15 | 1 | 1 |
| Cautery Cleaner | 2 | 0 |
| Cautery Pencil - Hand Control (Eclipse) | 2 | 0 |
| Drape Ioban Drape - 6650EZ | 1 | 0 |
| Dressing Steristrip 0.25 In × 4 In | 1 | 0 |
| Drape Ioban Steri-Drape - 6640 | 1 | 0 |
| Dressing Telfa 4 In × 8 In Strl | 1 | 0 |
| Glove Nitra-Touch Latex Free Sz 6.5 | 1 | 0 |
| Light Handle Set (3) | 1 | 0 |
| Needle Magnet | 1 | 0 |
| Pack Laparotomy/Abdominal Adult-Latex Free | 1 | 0 |
| Pad Grounding Cautery Adult | 1 | 0 |
| Set Laparatomy | 1 | 0 |
| Solution Benzoin Ampule | 1 | 0 |
| Solution Dura-Prep Sgl-Use | 1 | 1 |
| Sponge Lap 4 In × 18 In Prewshd Strl | 4 | 0 |
| Suture Prolene 1-0 CT-1 | 3 | 0 |
| Suture Vicryl 0 CT-2 | 2 | 0 |
| Syringe Asepto | 2 | 0 |
| Tegaderm - 4 × 4 ¾ | 1 | 0 |
| Tray Cath Foley w/Bag 16 Fr 5 cc | 1 | 0 |
| Tube Culturette Aerobic | 1 | 0 |
| Tube Culturette Anaerobic | 1 | 0 |

Since the patient is of average size, the defaults associated with patient size would not be changed. However, for a child or large adult, a number of the master items would be replaced with appropriately sized clinical items in the substitutions sets.

In a second example, the documentation aspect of the present invention is discussed relative to an exploratory laparotomy for two different patients. Patient A is a male with an allergy to iodine. Patient B is a female without any allergies.

Figure 6:
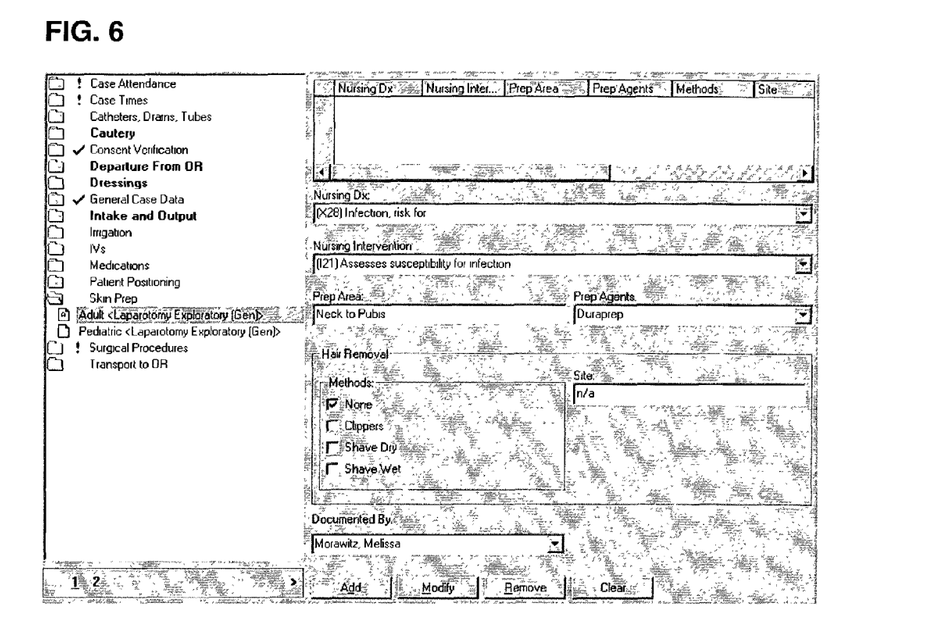
FIG. 6 is a first graphical user interface displaying documentation segments for a first exemplary patient.

With reference to FIG. 2A, scheduling information about the procedure and performing clinician is received at step 30. Next, at step 32, a preference card is identified based on the scheduling information. With reference to FIG. 6, a documentation segment for skin preparation from the identified preference card is shown. In the defaulted documentation segment, the preference card has a default value of "Neck to Pubis" for "Prep Area" (or Preparation Area). The default value for the "Prep Agent" (or Preparation Agent) is "Duraprep" and the default value for "Hair Method" is "None".

Figure 7:
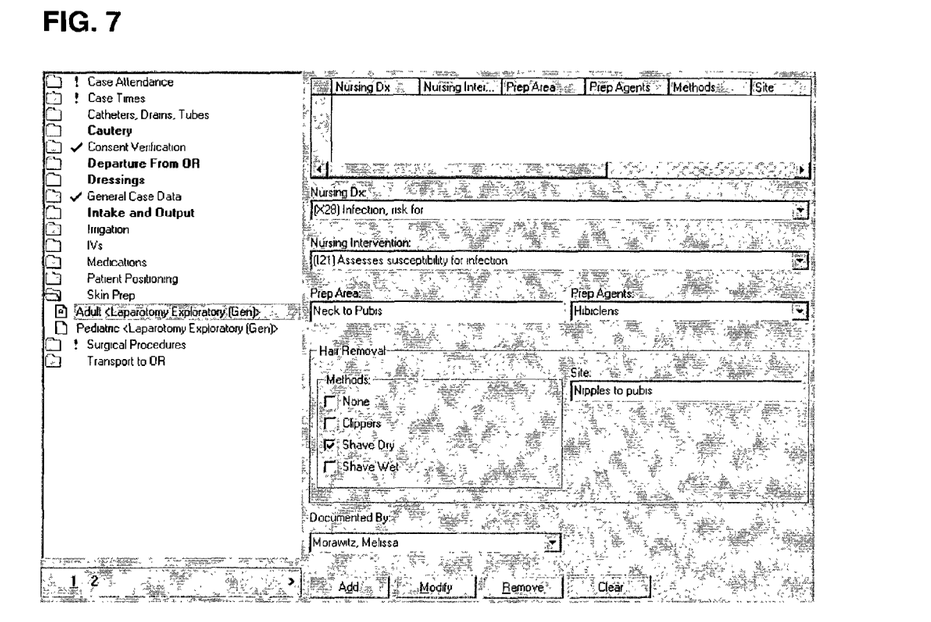
FIG. 7 is a second graphical user interface displaying the documentation segments for a second exemplary patient.

For Patient A, a rule would be accessed at step 55 to determine if a patient is allergic to latex. Technically, the rule would be satisfied if the patient's electronic record had a patient-specific value of "DURAPREP" that matched a predefined test value of "DURAPREP" for the allergy data value type. Since the electronic medical record for Patient A includes this value, the rule is satisfied at step 56. Then, at step 60, the substitution set for the satisfied rule would be accessed. The substitution set for this rule includes a master item having a value for "DURAPREP" and a substitution item having a value for "HIBICLENS"—an alternative agent to prepare the patient. With reference to FIG. 7, at step 62, the value for "HIBICLENS" replaces the value for "DURAPREP" in the documentation segment. Once the substitution set is applied, the remaining steps of the method of the present invention are performed by the system.

Likewise, a rule is accessed to determine if a patient is female. The substitution set includes values to change the default for the method of hair removal. Since Patient B is female, the rule is satisfied. In this instance, the master item of the substitution set is a value for "NO" or "NONE" for the method for hair removal and "NOT APPLICABLE" or "N/A" for the site, and the replacement items are "SHAVE DRY" for the method for hair removal and "NIPPLES TO PUBIS" for the site, respectively. Once the substitution set is applied, the pick list and documentation would be generated at step 58 and the subsequent steps are performed.

In addition to the examples set forth above, the substitution sets may replace all of the defaults in a single documentation segment with substituted items. Additionally, in some cases, the substitution set may completely eliminate a documentation segment or add additional documentation segments. In another example, an entire preference card could replace the defaulted preference card.

Although the invention has been described with reference to the preferred embodiment illustrated in the attached drawing figures, it is noted that substitutions may be made and equivalents employed herein without departing from the scope of the invention as recited in the claims. For example, additional steps may be added and steps omitted without departing from the scope of this invention.

What the invention claimed is:

1. A method in a computer system for preparing for a clinical event associated with a patient, comprising the steps of:
   identifying, through a first computing process, a preference card that is associated with an individual patient, a particular clinician, and a particular type of clinical event, wherein the particular clinician is scheduled to perform the particular type of clinical event on the individual patient, the preference card including a list of predefined clinical item values associated with one or more clinical items to be gathered for use for the clinical event, wherein the one or more clinical items include a plurality of non-medications;
   accessing, a second computing process, at least one patient-specific demographic value associated with the individual patient;
   determining, through a third computing process, whether at least one of the predefined clinical item values is incompatible with the at least one patient-specific demographic value; and
   without user intervention, updating, through a fourth computing process, the preference card by substituting, without user intervention, a compatible clinical item value for the at least one incompatible clinical item value if the at least one of the predefined clinical item values is incompatible with the at least one patient-specific demographic value, wherein the first, second, third, and fourth computing processes are performed on one or more computing devices.

2. The method of claim 1, further comprising the step of removing the at least one incompatible clinical item value from the preference card.

3. The method of claim 1, wherein a plurality of patient-specific demographic values are accessed from an electronic medical record.

4. The method of claim 1, wherein the preference card includes at least one documentation segment, the documentation segment having a plurality of documentation values, wherein the at least one documentation segment describes a preparation area on the individual patient.

5. The method of claim 4, further comprising the step of determining whether at least one of the documentation values is incompatible with at least one patient-specific demographic value.

6. The method of claim 5, further comprising the step of substituting a compatible documentation value for the incompatible documentation value.

7. The method of claim 5, further comprising the step of substituting a substitute documentation segment for the documentation segment having an incompatible documentation value.

8. The method of claim 1, wherein a plurality of compatible clinical item values are substituted for a plurality of incompatible clinical item values.

9. The method Of claim 1, wherein the patient-specific demographic value represents whether the patient has an allergy.

10. The method of claim 1, wherein the patient-specific demographic value represents the age, gender or weight of the patient.

11. The method of claim 1, wherein the clinical event is a surgical procedure.

12. A method in a computer system for preparing for a clinical event associated with a patient, comprising the steps of:
   receiving, through a first computing process, scheduling information;
   identifying, through a second computing process, a preference card that is associated with an individual patient, a particular clinician, and a particular type of clinical event, wherein the particular clinician is scheduled to perform the particular type of clinical event on the individual patient, the preference card associated with the scheduling information, the preference card also including a list of predefined values associated with one or more clinical items to be gathered for use for the clinical event, wherein the one or more clinical items include a plurality of non-medications;

accessing, through a third computing process, a plurality of patient-specific values for the individual patient;

determining, through a fourth computing process, whether at least one of the predefined values is incompatible with at least one patient-specific value; and without user intervention, updating, through a fifth computing process, the preference card by substituting, without user intervention, a compatible predefined value for the at least one incompatible predefined value if the at least one of the predefined values is incompatible with the at least one patient-specific value, wherein the first, second, third, fourth, and fifth computing processes are performed on one or more computing devices.

13. The method of claim 12, wherein the patient-specific values include demographic values.

14. The method of claim 12, wherein the scheduling information identifies the type of clinical event and clinician for the patient.

15. The method of claim 12, wherein at least one of the predefined values is a clinical item value, and further comprising the step of substituting a compatible clinical item value for the at least one incompatible clinical item value.

16. The method of claim 12, further comprising the step of removing the at least one incompatible clinical item value from the preference card.

17. The method of claim 12, wherein a plurality of patient-specific values are accessed from an electronic medical record.

18. The method of claim 12, wherein at least one of the predefined values is a documentation value, wherein the documentation value describes a position of the individual patient during the clinical event.

19. The method of claim 18, further comprising the step of substituting a compatible documentation value for the at least one incompatible documentation value.

20. The method of claim 12, wherein the patient-specific value represents whether the patient has an allergy.

21. The method of claim 12, wherein the patient-specific value represents the age, gender or weight of the patient.

22. The method of claim 12, wherein the clinical event is a surgical procedure.

23. A method in a computer system for preparing for a surgical procedure associated with a patient, comprising the steps of:

receiving, through a first computing process, scheduling information;

identifying, through a second computing process, a first preference card that is associated with an individual patient, a particular clinician, and a particular type of surgical procedure, wherein the particular clinician is scheduled to perform the particular type of surgical procedure on the individual patient associated with the scheduling information, the preference card including a list of predefined values associated with one or more clinical items to be gathered for use for the surgical procedure and at least one documentation segment, the documentation segment having a plurality of documentation values, wherein the document segment describes a preparation area on the patient, and wherein the one or more clinical items include a plurality of non-medications;

accessing, through a third computing process, a plurality of patient-specific demographic values for the individual patient;

determining whether at least one of the predefined values is incompatible with at least one patient-specific demographic value; and without user intervention, updating, through a fourth computing process, the preference card by substituting, without user intervention, a compatible predefined value for the at least one incompatible predefined value if the at least one of the predefined values is incompatible with the at least one patient-specific demographic value, wherein the first, second, third, and fourth computing processes are performed on one or more computing devices.

24. The method of claim 23, wherein the first preference card is replaced by a second preference card.

25. The method of claim 23, further comprising the step of determining whether at least one of the documentation values is incompatible with at least one patient-specific demographic value.

26. The method of claim 25, further comprising the step of substituting a compatible documentation value for the incompatible documentation value.

27. The method of claim 25, further comprising the step of substituting a substitute documentation segment for the documentation segment having an incompatible documentation value.

28. One or more non-transitory computer-storage media having computer-executable instructions embodied thereon that when executed by a computing device performs a method for preparing for a clinical event associated with a patient, comprising:

identifying a preference card that is associated with an individual patient, a particular clinician, and a particular type of clinical event, wherein the particular clinician is scheduled to perform the particular type of clinical event on the individual patient, the preference card including a list of predefined clinical item values associated with one or more clinical items to be gathered for use for the clinical event, wherein the one or more clinical items include a plurality of non-medications, and wherein the clinical event consists of one or more of a surgical procedure, examination, evaluation, and a test;

accessing at least one patient-specific demographic value for the individual patient;

determining whether at least one of the predefined clinical item values is incompatible with the at least one patient-specific demographic value; and updating without user intervention, the preference card by substituting, without user intervention, a compatible clinical item value for the at least one incompatible clinical item value if the at least one of the predefined clinical item values is incompatible with the at least one patient-specific demographic value.

29. The media of claim 28, wherein the method further comprises removing the at least one incompatible clinical item value from the preference card.

30. The media of claim 28, wherein a plurality of patient-specific demographic values are accessed from an electronic medical record.

31. The media of claim 28, wherein the preference card includes at least one documentation segment, the documentation segment having a plurality of documentation values.

32. The system media of claim 31, wherein the method further comprises determining whether at least one of the documentation values is incompatible with at least one patient-specific demographic value.

33. The media of claim 32, wherein the method further comprises substituting a compatible documentation value for the incompatible documentation value, wherein the documentation value describes a position of the individual patient during the clinical event.

34. The media of claim 32, wherein the method further comprises substituting a substitute documentation segment for the documentation segment having an incompatible documentation value.

35. The media of claim 28, wherein a plurality of compatible clinical item values are substituted for a plurality of incompatible clinical item values.

36. The media of claim 28, wherein the patient-specific demographic value represents whether the patient has an allergy.

37. The media of claim 28, wherein the patient-specific demographic value represents the age, gender or weight of the patient.

38. One or more non-transitory computer-storage media having computer-executable instructions embodied thereon that when executed by a computing device performs a method for preparing for a clinical event associated with a patient, comprising:
  receiving scheduling information;
  identifying component a preference card that is associated with an individual patient, a particular clinician, and a particular type of clinical event, wherein the particular clinician is scheduled to perform the particular type of clinical event on the individual patient, the preference card associated with the scheduling information, the preference card also including a list of predefined values associated with one or more clinical items to be gathered for use for the clinical event, wherein the one or more clinical items includes a plurality of non-medications;
  accessing a plurality of patient-specific values for the individual patient;
  determining whether at least one of the predefined values is incompatible with at least one patient-specific value; and
  updating, without user intervention, the preference card by substituting, without user intervention, a compatible predefined value for the at least one incompatible predefined value if the at least one of the predefined values is incompatible with the at least one patient-specific value.

39. The media of claim 38, wherein the patient-specific values include demographic values.

40. The media of claim 38, wherein the scheduling information identifies the type of clinical event and clinician for the patient.

41. The media of claim 38, wherein at least one of the predefined values is a clinical item value, and wherein the method further comprises substituting a compatible clinical item value for the at least one incompatible clinical item value.

42. The media of claim 38, wherein the method further comprises removing the at least one incompatible clinical item value from the preference card.

43. The media of claim 38, wherein a plurality of patient-specific values are accessed by the accessing component from an electronic medical record.

44. The media of claim 38, wherein at least one of the predefined values is a documentation value, wherein the documentation value describes a position of the individual patient during the clinical event.

45. The media of claim 44, wherein the method further comprises substituting a compatible documentation value for the at least one incompatible documentation value.

46. The media of claim 38, wherein the patient-specific value represents whether the patient has an allergy.

47. The media of claim 38, wherein the patient-specific value represents the age, gender or weight of the patient.

48. The media of claim 38, wherein the clinical event is a surgical procedure.

49. One or more non-transitory computer-storage media having computer-executable instructions embodied thereon that when executed by a computing device performs a method for preparing for a surgical procedure associated with a patient, comprising:
  receiving scheduling information;
  identifying a first preference card that is associated with an individual patient, a particular clinician, and a particular type of surgical procedure, wherein the particular clinician is scheduled to perform the particular type of surgical procedure on the individual patient, the preference card associated with the scheduling information, the preference card also including a list of predefined values associated with one or more clinical items to be gathered for use for the surgical procedure, wherein the one or more clinical items include a plurality of non-medications;
  accessing a plurality of patient-specific demographic values for the individual patient;
  determining whether at least one of the predefined values is incompatible with at least one patient-specific demographic-value; and
  updating, without user intervention, the preference card by substituting, without user intervention, a compatible predefined value for the at least one incompatible predefined value if the at least one of the predefined values is incompatible with the at least one patient-specific demographic value.

50. The media of claim 49, wherein the updating component replaces the first preference card with a second preference card.

51. The media of claim 49, wherein the preference card includes at least one documentation segment, the documentation segment having a plurality of documentation values.

52. The media of claim 51, wherein the method further comprises determining whether at least one of the documentation values is incompatible with at least one patient-specific demographic value, wherein the documentation value describes a position of the individual patient during the clinical event.

53. The media of claim 52, wherein the method further comprises substituting a compatible documentation value for the incompatible documentation value.

54. The media of claim 52, wherein the method further comprises substituting documentation segment for the documentation segment having an incompatible documentation value.

55. One or more non-transitory computer-storage media containing instructions, that when executed by a computing device, performs a method for controlling a computer system for preparing for a clinical event associated with a patient, by:
  identifying a preference card that is associated with an individual patient, a particular clinician, and a particular type of clinical event, wherein the particular clinician is scheduled to perform the particular type of clinical event on the individual patient, the preference card including a list of predefined clinical item values associated with one or more clinical items to be gathered for use for the clinical event,
  wherein the one or more clinical items include a plurality of non-medications, wherein the clinical event consists of one or more of a surgical procedure, examination, evaluation, and a test, and wherein the preference card includes at least one documentation segment, the documentation segment having a plurality of documentation values;

accessing at least one patient-specific demographic value for the individual patient;

determining whether at least one of the documentation values is incompatible with the at least one patient-specific demographic value, wherein the documentation value describes a position of the individual patient during the clinical event;

without user intervention, updating the preference card by substituting a compatible documentation value for the incompatible documentation value if the at least one of the documentation values is incompatible with the at least one patient-specific demographic value;

determining whether at least one of the predefined clinical item values is incompatible with the at least one patient-specific demographic value; and without user intervention, updating the preference card by substituting, without user intervention, a compatible clinical item value for the at least one incompatible clinical item value if the at least one of the predefined clinical item values is incompatible with the at least one patient-specific demographic value.

56. The media of claim 55, further comprising the step of removing the at least one incompatible clinical item value from the preference card.

57. The media of claim 55, wherein a plurality of patient-specific demographic values are accessed from an electronic medical record.

58. The media of claim 55, further comprising the step of substituting a substitute documentation segment for the documentation segment having an incompatible documentation value.

59. The media of claim 55, wherein a plurality of compatible clinical item values are substituted for a plurality of incompatible clinical item values.

60. The media of claim 55, wherein the patient-specific demographic value represents whether the patient has an allergy.

61. The media of claim 55, wherein the patient-specific demographic value represents the age, gender or weight of the patient.

62. One or more non-transitory computer-storage media containing instructions, that when executed by a computing device, performs a method for controlling a computer system for preparing for a clinical event associated with a patient, by:

receiving scheduling information;

identifying a preference card that is associated with an individual patient, a particular clinician, and a particular type of clinical event, wherein the particular clinician is scheduled to perform the particular type of clinical event on the individual patient, the preference card associated with the scheduling information, the preference card also including a list of predefined values associated with one or more clinical items to be gathered for use for the clinical event, wherein the one or more clinical items include a plurality of non-medications;

accessing a plurality of patient-specific values for the individual patient;

determining whether at least one of the predefined values is incompatible with at least one patient-specific value; and without user intervention, updating the preference card by substituting, without user intervention, a compatible predefined value for the at least one incompatible predefined value if the at least one of the predefined values is incompatible with the at least one patient-specific value.

63. The media of claim 62, wherein the patient-specific values include demographic values.

64. The media of claim 62, wherein the scheduling information identifies the type of clinical event and clinician for the patient.

65. The media of claim 62, wherein at least one of the predefined values is a clinical item value, and further comprising the step of substituting a compatible clinical item value for the at least one incompatible clinical item value.

66. The media of claim 62, further comprising the step of removing the at least one incompatible clinical item value from the preference card.

67. The media of claim 62, wherein a plurality of patient-specific values are accessed from an electronic medical record.

68. The media of claim 62, wherein at least one of the predefined values is a documentation value.

69. The media of claim 68, further comprising the step of substituting a compatible documentation value for the at least one incompatible documentation value.

70. The media of claim 62, wherein the patient-specific value represents whether the patient has an allergy.

71. The media of claim 62, wherein the patient-specific value represents the age, gender or weight of the patient.

72. One or more non-transitory computer-storage media containing instructions, that when executed by a computing device, performs a method controlling a computer system for preparing a surgical procedure associated with a patient, by:

receiving scheduling information;

identifying a first preference card that is associated with an individual patient, a particular clinician, and a particular type of surgical procedure, wherein the particular clinician is scheduled to perform the particular type of surgical procedure on the individual patient associated with the scheduling information, the preference card including a list of predefined values associated with one or more clinical items to be gathered for use for the surgical event, wherein the one or more clinical items includes a plurality of non-medications;

accessing a plurality of patient-specific demographic values for the individual patient;

determining whether at least one of the predefined values is incompatible with the at least one demographic patient-specific value; and without user intervention, updating the preference card by substituting, without user intervention, a compatible predefined value for the at least one incompatible predefined value if the at least one of the predefined values is incompatible with the at least one patient-specific demographic value.

73. The media of claim 72, wherein the first preference card is replaced by a second preference card.

74. The media of claim 72, wherein the preference card includes at least one documentation segment, the documentation segment having a plurality of documentation values.

75. The media of claim 74, further comprising the step of determining whether at least one of the documentation values is incompatible with at least one patient-specific demographic value.

76. The media of claim 75, further comprising the step of substituting a compatible documentation value for the incompatible documentation value.

77. The media of claim 75, further comprising the step of substituting a substitute documentation segment for the documentation segment having an incompatible documentation value.

* * * * *